(12) United States Patent
Kolluri et al.

(10) Patent No.: US 7,831,300 B2
(45) Date of Patent: Nov. 9, 2010

(54) EXTRAPOLATING ICA KNOWLEDGE FROM ONE EPOCH TO ANOTHER FOR IMPROVED FETAL ECG SEPARATION

(75) Inventors: Sai Kolluri, Tampa, FL (US); Bruce A. Friedman, Tampa, FL (US); Lawrence T. Hersh, Tampa, FL (US); Rush Winslow Hood, Jr., Tampa, FL (US)

(73) Assignee: The General Electric Company, Schenectady, NY (US)

( * ) Notice: Subject to any disclaimer, the term of this patent is extended or adjusted under 35 U.S.C. 154(b) by 330 days.

(21) Appl. No.: 12/034,129

(22) Filed: Feb. 20, 2008

(65) Prior Publication Data

US 2009/0209874 A1    Aug. 20, 2009

(51) Int. Cl.
*A61B 5/0245* (2006.01)
(52) U.S. Cl. .................................................... 600/511
(58) Field of Classification Search .............. 607/511; 600/508–526
See application file for complete search history.

(56) References Cited

U.S. PATENT DOCUMENTS

| 2004/0243015 A1 | 12/2004 | Smith et al. |
| 2005/0267376 A1 | 12/2005 | Marossero et al. |
| 2005/0267377 A1 | 12/2005 | Marossero et al. |
| 2006/0189882 A1 | 8/2006 | Thomas |
| 2007/0088226 A1 | 4/2007 | Spence et al. |

FOREIGN PATENT DOCUMENTS

| EP | 1844706 A1 | 10/2007 |
| WO | 03/003905 A2 | 1/2003 |

OTHER PUBLICATIONS

Arani et al., "Extracting Uncontaminated Neural Signals Using Independent Component Analysis", University of California, San Diego, pp. 1-2.
Graupe et al., "Extraction of Fetal ECG from Maternal ECG Early in Pregnancy", IJBEM, vol. 7, No. 1, 2005, pp. 166-168.

(Continued)

*Primary Examiner*—Scott M Getzow
*Assistant Examiner*—Amanda Patton
(74) *Attorney, Agent, or Firm*—Andrus, Sceales, Starke & Sawall, LLP

(57) ABSTRACT

A method of utilizing a maternal-fetal monitoring system to monitor the physiological properties of both a maternal patient and a fetus. A series of ECG electrodes are placed across the maternal patient's abdomen and receives ECG input waveforms across sixteen separate channels. The sixteen channels of information are processed using an ICA algorithm to generate a series of ICA output waveforms and a transfer matrix. Following the current epoch, the transfer matrix is applied to the input waveforms on a continuous basis. The conditioned input waveforms are displayed immediately following the first epoch and prior to the expiration of a subsequent epoch. The transfer matrix for the second epoch is combined with the transfer matrix for the first epoch to generate an updated transfer matrix. Various filtering operations on the transfer matrix coefficients may be used to find the updated transfer matrix before the end of the current epoch.

18 Claims, 4 Drawing Sheets

OTHER PUBLICATIONS

He et al., "Application of ICA in Removing Artefacts from the ECG", Dept. of Engineering Science, University of Oxford, Oxford, UK, pp. 1-18.

Martens et al., "A robust fetal ECG detection method for abdominal recordings", Physiological Measurement 28 (Mar. 7, 2007), IOP Publishing Ltd., pp. 373-388.

Search Report dated May 13, 2009.

EXTRAPOLATING ICA KNOWLEDGE FROM ONE EPOCH TO ANOTHER FOR IMPROVED FETAL ECG SEPARATION

FIELD OF THE INVENTION

The present disclosure generally relates to a method of non-invasively monitoring the heartbeat and ECG of an unborn fetus. More specifically, the present disclosure relates to a method of processing and identifying fetal ECG signals from a multi-channel electrocardiogram (ECG) obtained from a maternal patient and continuously displaying the fetal ECG signal.

BACKGROUND OF THE INVENTION

An electrocardiogram (ECG) is a very important tool in the diagnosis of heart disease and abnormalities in both children and adults. The new signal processing and detection capabilities provided when using maternal abdominal ECG electrodes provides access to the ECG of unborn children. The use of a fetal ECG (fECG) can lead to the early detection and monitoring of heart abnormalities that can be treated, which in turn leads to better fetal health.

However, obtaining an accurate fetal ECG is difficult due to the weaker fetal electrical signals obtained from the abdomen of the mother. Specifically, when multiple ECG electrodes are placed on the abdomen of the mother to gather the required ECG information, several obvious problems arise. The first is that the mother's ECG is present and is usually significantly larger than the ECG of the fetus. Second, if monitoring is being done late in pregnancy, uterine contractions may be present, which result in large electrical artifacts that obliterate or mask the fetal signal. Third, in many cases, the mother is experiencing discomfort and is unable to lie still, which creates large electrical muscle artifacts.

Presently, signal processing techniques exist, including the use of independent component analysis (ICA) algorithms that can be applied to the input ECG signals obtained from the mother to provide clean waveforms that can be further processed. The output signals from the ICA algorithm can be further processed to provide information relating to the maternal and fetal heart rate, maternal and fetal ECG intervals, and uterine contraction intensity and episodes. In application, the input signals to the ICA algorithm contain combinations of the signals from these various sources. The purpose of the ICA is to separate these sources so that the desired information about each source can be identified. The output of the ICA algorithm will provide at least one channel waveform for each source. Typically, the ICA algorithm is performed using the entire set of input channels over an epoch having a pre-determined time duration, such as 4-5 seconds. Although ICA algorithms can separate fetal ECG, maternal ECG, and uterine waveforms for a specific epoch, the ICA algorithms must be conducted over an epoch having a specific period. Therefore, for example, the fetal ECG information and waveform displayed on a monitor represents the ECG information and waveform for the fetus over the previous epoch. Since the ICA algorithm requires input waveforms recorded over an epoch to calculate the output ICA waveforms, the ECG information derived for a fetus is delayed prior to display. Further, the ICA algorithm does not guarantee that the output signal associated with a particular source is on the same ICA output channel from epoch to epoch Therefore, a need exists to provide for continuous display of the fetal ECG information and waveform without requiring the delay period of the epoch and without requiring channel sorting for each new ICA epoch output. This means that a method of processing an epoch, at least temporarily during its acquisition, would be useful. After an epoch is completely obtained it can be further processed as usual to optimize source separation and channel sorting before moving on to subsequent epochs for display and monitoring.

BRIEF DESCRIPTION OF THE DISCLOSURE

The present disclosure generally relates to a method of monitoring maternal and fetal vital signs, including ECG and heart rate information, obtained from a maternal patient. More specifically, the present disclosure relates to a method of utilizing information relating to the fetal and maternal ECG signals determined from one epoch to continuously determine and display information during a subsequent epoch.

Initially, a plurality of ECG electrodes are placed on the abdomen of a maternal patient to obtain ECG signals. The electrodes are connected such that a set of input channel waveforms can be obtained for the monitoring device.

During the initial period of operation of the ECG monitoring device, the plurality of input waveforms from the electrodes applied to the abdomen are stored for a first epoch. Once the input waveforms have been stored for the first epoch, an independent component analysis (ICA) algorithm is applied to the set of waveforms over the defined epoch. Typically, the defined epoch is between four and five seconds in duration such that the ICA algorithm is applied to the waveforms over the entire duration of the epoch. Various methods of implementing the ICA algorithm are well known and widely available to those skilled in the art.

During the application of the ICA algorithm to the stored input waveforms, the ICA algorithm generates a plurality of ICA output waveforms and a first transfer matrix. The first transfer matrix is able to convert the samples of the input ECG waveforms at any particular instant of the epoch and convert them into the samples of the ICA output waveforms. Mathematically, this operation is a matrix multiplication:

$$y_i = \sum_j T_{ij} \cdot x_j,$$

where T is the transfer matrix, i is the output channel index, and j is the input signal index. y is a vector representing the sample of the output waveforms and x is a vector representing the samples of input waveforms. This equation represents the ICA transformation at one instant in time. The ICA algorithm provides the transfer matrix T for the relevant epoch. When the transfer matrix T is applied to all instants of time for the epoch, the source separated waveforms are determined.

After the first transfer matrix has been calculated for the first epoch, the first transfer matrix is applied to the input waveforms received from the maternal abdomen following the first epoch. Based upon an assumption that the fetal signal and the maternal signal do not change channels immediately from the first epoch to the second epoch, the transfer matrix calculated during the first epoch is applied to the input waveforms to generate a plurality of conditioned waveforms. In this manner, the system and method of the present disclosure utilizes the transfer matrix calculated during a previous epoch to condition the input waveforms for a period of time following the first epoch. Preferably, the transfer matrix from the previous epoch is applied to the input waveforms continuously such that the input waveforms are continuously conditioned. Once the input waveforms have been conditioned, the input waveforms can be displayed on a continuous basis following the first epoch.

After the first epoch, the input waveforms are stored for a second epoch. Once the second epoch has been completed, the system and method applies the ICA algorithm to the input waveforms stored for the second epoch. The application of the ICA algorithm for the second epoch results in a second set of ICA output waveforms and a second transfer matrix.

Once the second transfer matrix has been calculated, the first and second transfer matrices are combined to generate an updated transfer matrix that is based upon both the first and second transfer matrices. One possible way to update the transfer matrix being used for determining the latest display samples would be to calculate an average of the coefficients of the first and second transfer matrices. Other combining techniques can also be used. It may be necessary to sort the output channels so that the independent source signals are in the same output channel positions before combining the transfer matrices from the two epochs. Correlation patterns in the transfer matrix coefficients themselves may aid in doing this sorting. Possible and proper ways of using the transfer matrix from past epochs to develop an updated transfer matrix for the present epoch before the present epoch is completed is one feature of the disclosed method.

Once the updated transfer matrix has been calculated following the expiration of the second epoch, the updated transfer matrix is utilized by the system and method to condition the input waveforms for the period of time immediately following expiration of the second epoch. In this manner, the updated transfer matrix is based upon the two most previous epochs and is utilized to condition input waveforms being received during the next, third epoch. In this manner, the input waveform obtained from a maternal abdomen can be conditioned on a real-time, continuous basis and displayed to a clinician.

In yet another embodiment of the present disclosure, the system and method determines which of the output channels are from the maternal, fetal, and uterine signal sources. Based upon the determination of which output channel corresponds to a particular source, the system and method of the present disclosure displays selected waveforms from the patient. Specifically, the system displays either the conditioned fetal signal or the conditioned maternal signal, or both. The maternal and fetal signals can be displayed on a continuous basis utilizing the system and method of the present disclosure rather than waiting for the expiration of the then-current epoch to display the ECG signals for both the fetus and the maternal patient.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
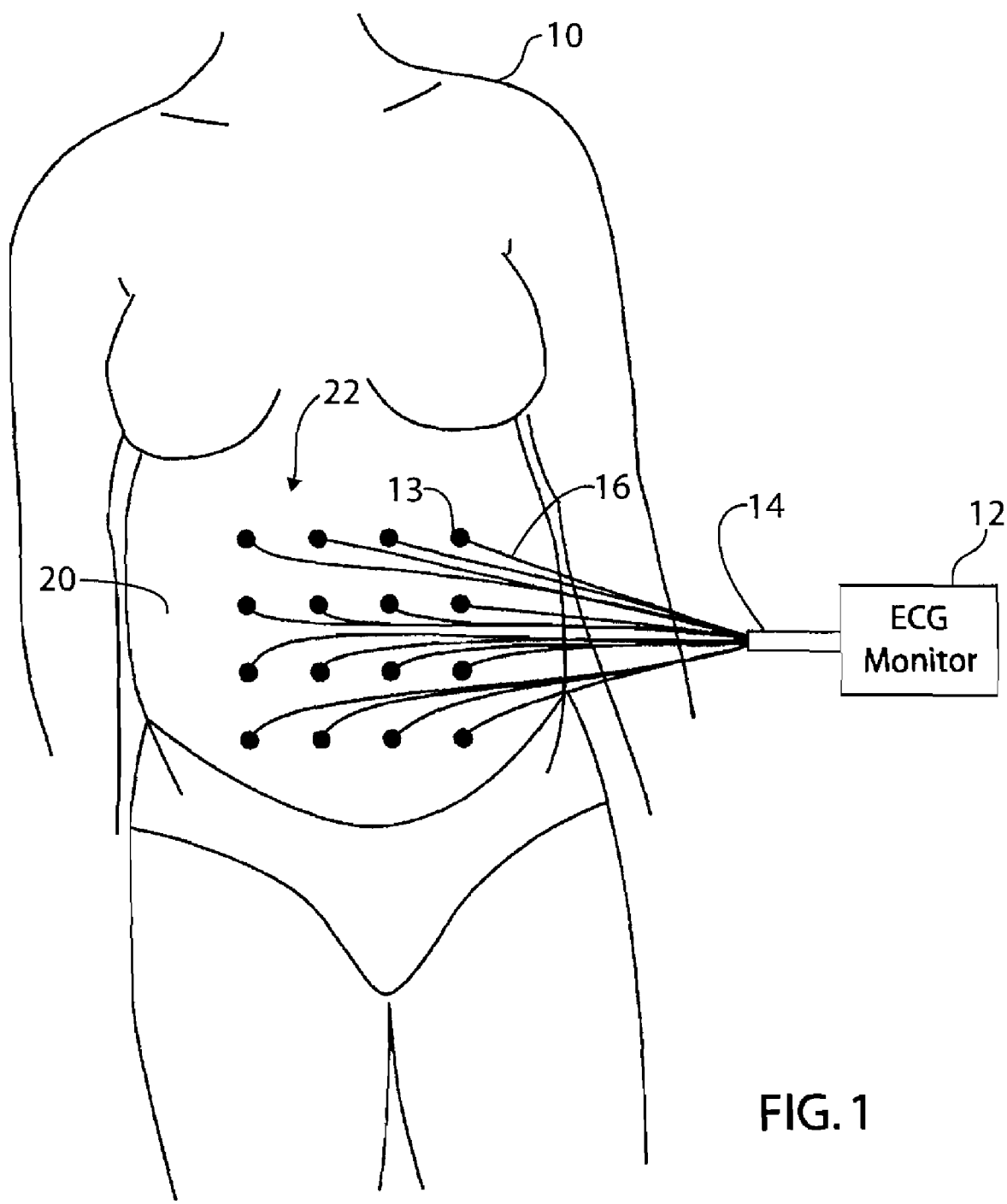
FIG. 1 is an illustration of a set of ECG electrodes positioned on an abdomen of a maternal patient in accordance with the present disclosure.

FIG. 1 illustrates a maternal patient 10 connected to an ECG monitor 12 such that the ECG monitor 12 can monitor both physiological data from the patient 10 as well as a fetus (not shown) being carried by the patient 10. As illustrated in FIG. 1, the ECG monitor 12 receives a sensor cable 14 that includes individual channels or leads 16 each connected to an electrode 18 attached to the abdomen 20 of the patient 10. In the embodiment shown in FIG. 1, the sensor cable 14 includes sixteen separate ECG electrodes 18 that are positioned in an array 22 spaced on the mother's abdomen 20. In addition to the sixteen ECG electrodes 18, the sensor cable 14 can also include a ground electrode and a reference electrode, as is conventional when recording ECG measurements from a patient 10. Although the electrode placement shown in FIG. 1 is in a general four-by-four array, various other electrode arrangements can be utilized while operating within the scope of the present disclosure.

In order to achieve good separation, the abdominal ECG electrodes 18 should not be placed too close together and should involve a wide coverage of the abdomen. Typically, the regularly spaced sixteen electrodes are spaced over the entire skin surface of the patient 10. Each of the ECG electrodes 18 detects electrical signals present on the skin of the patient and returns the sensed electrical signals to the ECG monitor 12 over the series of separate patient leads 16.

As will be described in much greater detail below, the ECG monitor 12 obtains a separate input waveform from each of the ECG electrodes 18 of the abdominal array. The ECG monitor 12 includes operating programs and software, to be described in much greater detail below, that operate to separate the input ECG channel waveforms into waveforms that are generated from independent maternal heart, fetal heart, uterine contraction and noise sources and from which physiological information relating to the mother and the fetus can be derived and displayed. As used throughout the remaining portions of this disclosure, the physiological properties for both the mother and the fetus include at least maternal and fetal heart rate, respiratory rate, ECG results and EHG.

Figure 2:
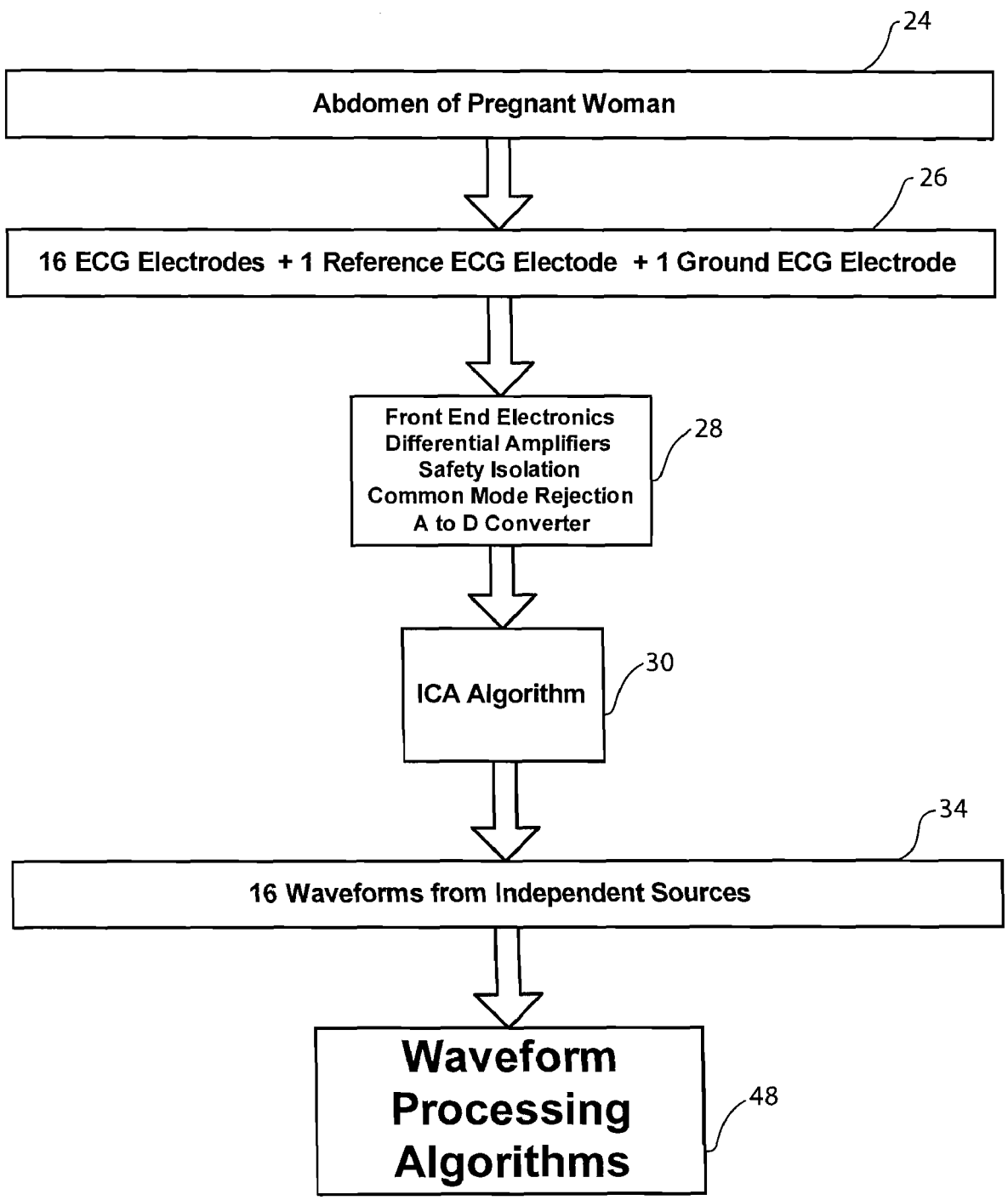
FIG. 2 is a data flow diagram of the method of the present disclosure that utilizes an ICA algorithm applied to fetal ECG extraction.

Referring now to FIG. 2, the initial step in the method of the present disclosure is to prepare the abdomen of a pregnant patient for the application of the array of electrodes, as illustrated in step 24. This preparation typically includes removing clothing covering the abdomen 20 and cleaning the abdomen to prepare the skin for good surface contact with the individual ECG electrodes 18, as shown in FIG. 1. Referring back to FIG. 2, the next step in the method is to place the sixteen ECG electrodes, the one reference ECG electrode and the one ground ECG electrode on the patient, as set forth in step 26. Typically, each of the electrodes includes an adhesive that adheres the electrode to the patient's abdomen and creates the required skin to surface contact to sense electrical signals present on the outer skin surface of the patient due to electrical activity within both the mother and the fetus.

Once the individual electrodes 18 are placed on the patient's abdomen 20, sixteen separate, individual input waveforms are received at the ECG monitor through the sixteen leads 16 shown in FIG. 1. As shown in step 28 of FIG. 2, the ECG monitor 12 includes front end electronics, differential amplifiers, isolation devices and common mode rejection components that receive the individual input waveforms from the electrodes and provide for initial, conventional processing of the sixteen separate input waveforms received on the sixteen separate channels at the ECG monitor 12. Preferably, the ECG monitor includes computing and storage means for receiving the individual input waveforms and outputting monitoring data for use by a physician. Such digital instrumentation, as is well understood by skilled artisans, can process the input waveforms by applying algorithms and filtering operations. Further, the computing means can include storage components for recording the input waveforms, as will be described in detail below.

In the embodiment of the disclosure shown, the ECG monitor 12 provides initial processing of the input waveforms received across the sixteen separate channels and records the input waveform in memory contained within the ECG monitor. Since the input waveform for each channel is received continuously at the ECG monitor, the ECG monitor 12 stores the input waveforms continuously in a memory device contained within the ECG monitor.

As described previously, the input waveforms received across the sixteen channels connected to the ECG monitor 12 include noise and unwanted signal information. To clean up the input waveforms received directly from the ECG electrodes, the system and method shown in FIG. 2 utilizes blind source separation (BSS) using an independent component analysis (ICA) algorithm applied to the sixteen separate channels from the individual electrodes applied to the patient's abdomen. To apply the ICA algorithm shown in step 30, the ECG monitor stores the continuous input waveforms from each of the sixteen channels over a defined period of time.

The stored input waveforms for each of the sixteen channels connected to the ECG electrodes are stored and segmented into individual epochs. Typically, an epoch has a fixed duration such that signal processing techniques can be carried out on the input waveforms over the epoch. In the embodiment shown in the present disclosure, an epoch typically has a duration of approximately 4-5 seconds, although other durations are contemplated. It is preferred that each of the epochs have a duration that is greater than the heartbeat frequency for both the patient 10 and the fetus. An epoch duration of five seconds is shown in the embodiment of the present disclosure, as illustrated by the epoch duration 32 shown in FIG. 3.

Referring back to FIG. 2, the ICA algorithm is applied to each of the input waveforms at step 30 to generate clean and separate signals that represent the electrical activity of the mother, the fetus and any other independent sources that may be present during the acquisition over the sixteen ECG electrodes 18. The BSS/ICA data processing techniques of step 30 are well known to those of skill in the art and are readily available from numerous outlets. The ICA algorithm of step 30 is preferably implemented in real time on a computing means contained within the ECG monitor. The ICA algorithm filters the input waveforms received directly from the ECG electrodes such that the filtered waveforms can be further processed by other algorithm techniques to obtained desired physiological information. As described, ICA algorithms are well known and have been used for quite some time. As an example, the ICA algorithm could be any known BSS algorithm such as FASTICA or CUBICA, although other types of ICA algorithms are contemplated as being within the scope of the present disclosure. An example of the use of a BSS method based on ICA is described in "Extraction of Fetal ECG From Maternal ECG Early in Pregnancy", Daniel Graupe, Yunde Zhong, Menachem H. Graupe, IJBEM, Vol. 7, No. 1, 2005.

The input waveforms obtained from the sixteen different ECG channels are used by the ICA algorithm 30 to produce sixteen separate waveforms that are each assumed to be generated from separate and independent sources, as indicated in step 34. Since the ICA algorithm 30 separates noise sources and physiological sources, the sixteen ICA output waveforms, generated in step 34, can be utilized to determine on which channel the fetal and maternal ECG signal sources are present. Once the channels have been identified, further processing can be conducted on the maternal, fetal, and uterine signals to derive physiological information such as the heart rate.

Figure 3:
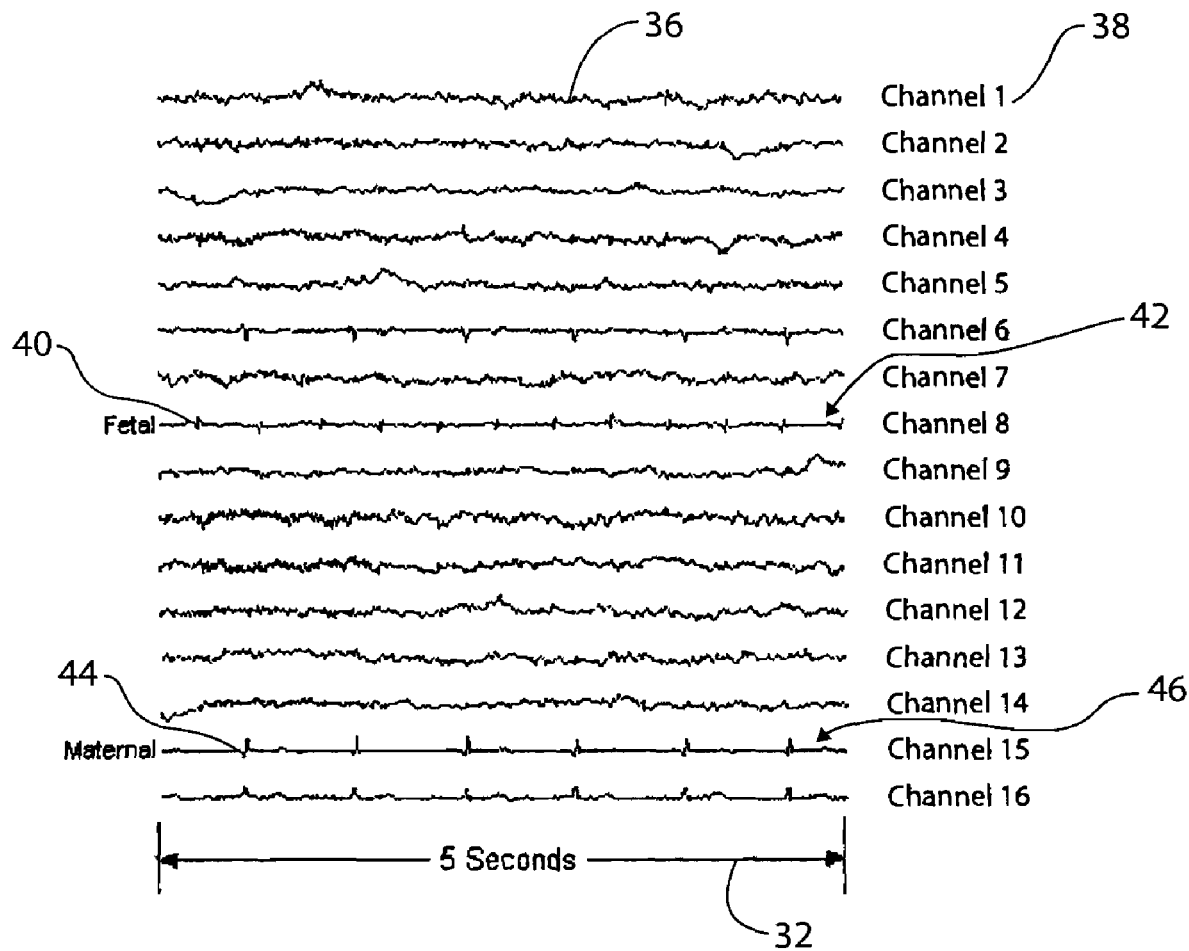
FIG. 3 is an example of ICA output waveforms from electrodes applied to the maternal abdomen.

Referring now to FIG. 3, thereshown are the ICA output waveforms 36 that are generated by the ICA algorithm shown in step 30 of FIG. 2. The ICA output waveforms 36 are present as sixteen channels 38 of ECG signals, where each channel 38 represents one of the plurality of sources that went into constructing the input waveforms. As can be seen in FIG. 3, many of the sixteen channels 38 shown in FIG. 3 include ICA output waveforms that appear to present only noise or signals having very little usefulness in monitoring the fetal and maternal ECGs and heart rates. However, as shown in the specific embodiment of FIG. 3, the ICA output waveform on channel 8 includes a series of signature QRS events 40 that represent the heartbeat and ECG signal from a fetal source. Thus, the fetal signal 42 for the epoch 32 is said to reside on channel 8.

Likewise, channel 15 includes a series of QRS events 42 that represent a heartbeat and ECG signal received from a maternal source. Thus, channel 15 from the epoch 32 is classified as a maternal signal 46. In addition to the QRS events 44, the material signal 46 also includes T-waves following the application of the ICA algorithm.

As can be understood in the plurality of ICA output waveforms shown in FIG. 3, the ICA output waveforms 36 can be utilized to determine significant physiological properties for both the maternal patient and the fetus. Specifically, the ICA output waveform 36 present on channel 15 can be utilized to determine physiological properties from the maternal patient, while the ICA output waveform present on channel 8 can be utilized to determine physiological properties for the fetus. This use of the ICA algorithm to generate the ICA output waveforms shown in FIG. 3 is generally well known and defined in the state of the art.

Referring back to FIG. 2, the next step in the method of the present disclosure is to utilize some type of waveform sorting algorithm 48 to identify which channels represent a maternal, fetal, or uterine signal source. Once the waveform sorting algorithm 48 determines which channels represent the maternal and fetal signal sources, the waveforms from these channels are fed to either a maternal ECG processor or a fetal ECG processor for further processing. The maternal ECG processor can determine physiological properties for the maternal patient using appropriate ICA output waveform, while the fetal ECG processor can perform processing techniques to generate physiological properties for the fetus.

During the application of the ICA algorithm to the input waveforms during the first epoch, the ICA algorithm is applied to the input waveforms over the entire duration of the epoch. As described, the ICA algorithm used is one from a family of related algorithms that perform blind source separation. The ICA algorithm assumes that the source components are statistically independent. The mathematical structure used by the ICA algorithm to relate the input waveforms to the output waveforms is the following:

$$y = T \cdot x$$

In the above equation, T is a square (n by n) transfer matrix applied in the time domain, where n is the number of raw input waveforms from the maternal abdomen. In the ICA algorithm, x and y are an n by m matrices, where m is the number of samples for the waveform and n is again the number of raw input waveforms from the maternal abdomen.

Based upon the above generalization of the ICA algorithm, y is the near independent sixteen output source waveforms created by the ICA algorithm.

As described above, the determination of the transfer matrix T is the essence of the ICA algorithm and requires a rather large amount of complex computations to determine for the specific epoch. The contents of the transfer matrix T depend upon the raw input waveforms and the statistical method being used to get to the independent output waveform state y. Once the transfer matrix T is obtained, the transfer matrix has an optimal value for the epoch from which it came.

In typical uses of an ICA algorithm, the ICA algorithm is applied to each separate epoch of a series of sequential epochs. Thus, before the ICA output waveforms can be generated, the ICA algorithm calculates a separate transfer matrix T for the then current epoch. Thus, for each epoch of a continuous series of epochs recorded from a maternal patient during monitoring, a transfer function is calculated for each epoch before the input waveforms are conditioned and displayed as ICA output waveforms. This delay in processing results in the display presented to a clinician being delayed by at least the length of an epoch. Since an epoch may have a duration of 5-10 seconds, the ECG information displayed to a clinician is delayed by at least the 5-10 second duration of the epoch.

One of the challenges in using an automated system to monitor and display a fetal ECG signal and a maternal ECG signal from the sixteen input channels attached to the electrode display on the maternal abdomen is that the fetal signal and the maternal signal can, and typically do, change channels from one epoch to another. Thus, although the location of the maternal and fetal signals may be determined for a first epoch, the maternal and fetal signals for the next epoch could be located on different channels. The movement of the maternal and fetal signals from one channel to another during the continuous monitoring may be due to various different factors, such as movement of the patient during monitoring, movement of the fetus during monitoring, or physical changes in the patient being monitored. Although it is known that maternal and fetal signals may change channels during monitoring, the present disclosure operates on the initial assumption that the fetal and maternal signals will not change channels from one epoch to another. This assumption allows for automated techniques of determining and displaying ECG signals from both the fetus and the maternal patient on a continuous basis. During the continuous monitoring, the system continues to determine which channels include the fetal and maternal signals and modifies the operation based upon these calculations. However, until the system determines that the maternal and fetal signals have changed channels, the system and method of the disclosure utilizes information calculated from a past epoch to condition the input waveforms received from the maternal patient.

Figure 4:
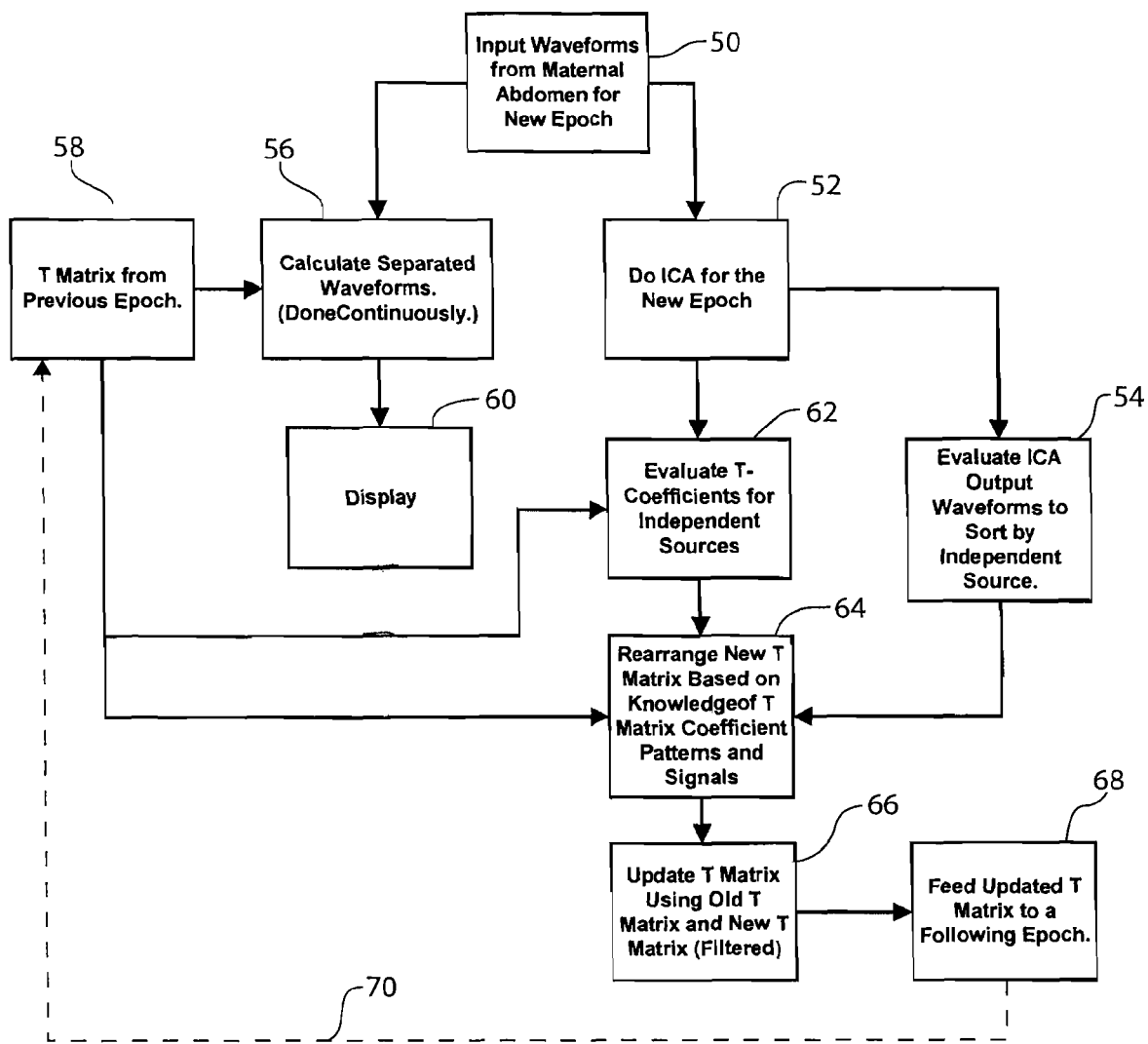
FIG. 4 is a flow chart illustrating the use of a transfer matrix calculated from a past epoch to calculate and display the ECG waveforms for the fetus.

The method of the present disclosure, as set forth in FIG. 4, utilizes the assumption that the transfer matrix calculated from a first epoch can be utilized to condition the input waveforms from the maternal abdomen following the first epoch and before the expiration of the second epoch. Specifically, the transfer matrix T calculated for the first epoch will have captured aspects of the geometrical arrangement of the abdominal electrodes as well as include information as to which of the plurality of channels includes a fetal signal and, possibly, the maternal signal. Thus, with this knowledge, the method of the present disclosure utilizes the transfer matrix T calculated from the first epoch on the input waveforms received during the next, second epoch. Throughout the description, the epochs will be referred to as a first epoch and a second epoch. It should be understood that these descriptions are meant to indicate that the first epoch ends at a specific moment in time while the second epoch ends at a moment in time that is after the end of first epoch. As an example, the first epoch may be recorded for seconds 0-10, while the second epoch will be recorded for the time duration extending from 10 seconds to 20 seconds, where the second epoch immediately follows the first epoch.

However, further note that there is nothing limiting the embodiment being disclosed herein from the epochs overlapping one another. For example, the first epoch could be defined as starting at 0 seconds and ending at 10 seconds, the second epoch starting at 5 seconds and ending at 15 seconds, the third epoch starting at 10 seconds and ending at 20 seconds and so forth. The amount of overlap could range from a single sample period to nearly the entire length of the epoch duration being used. In the following disclosure, the epochs are described as generally following one another in time for clarity, but should be considered only to relate to each other in time such that when one epoch finishes its transfer coefficients can be applied to the subsequent epoch even though in real time it may be well past the start of the subsequent epoch.

Referring now to FIG. 4, thereshown is a general flow diagram of the processing steps that occur utilizing the method of the present disclosure. As indicated in step 50, the system receives input waveforms from the maternal abdomen for the new, second epoch. Typically, the input waveforms received from the maternal abdomen are stored in a memory location within the ECG monitor for the duration of the epoch. As described previously, in the embodiment shown in the drawing figures, the epoch has a duration of five seconds, although other durations for the epoch are contemplated. In the embodiment shown in FIG. 4, the new epoch will be referred to as the second epoch, since the new epoch is assumed to take place after the previous, first epoch. However, as described above, the reference to first and second epochs are meant to only relate two separate epochs to each other in time.

Referring back to FIG. 2, during the first epoch, the ICA algorithm 30 generates the sixteen waveforms for the independent sources and generates a first transfer matrix in the manner described above. The first transfer matrix T is stored in a memory location within the ECG monitor for use as will be described below. When the ECG monitoring device operating in accordance with the methods of FIGS. 2 and 4 is operated for the first, initial epoch, the system and method utilizes the ICA algorithm 30 to calculate the first transfer matrix T. During the calculation of the first transfer matrix, the system and method cannot compare the first transfer matrix to any other transfer matrix stored in memory for the patient, since the first transfer matrix is assumed to be the initial transfer matrix calculated for the maternal patient. Thus, many of the comparison steps shown and described in FIG. 4 are not utilized for the initial, first epoch since the system does not include any stored transfer matrix prior to the calculation of the initial, first transfer matrix. However, as described above, the reference to the first and second epoch are only meant to relate separate epochs to each other in time, and are not meant to refer to the first and second epochs recorded from a patient from the beginning of the monitoring process.

Referring back to FIG. 4, upon receipt of the input waveforms from the abdomen of the maternal patient for the second epoch following the first epoch, the system conducts the ICA algorithm on the input waveforms for the second epoch, as illustrated in step 52. Once the ICA algorithm has been applied to the input waveforms during the second epoch, the system evaluates the ICA output waveforms in step 54. In step 54, the system determines which of the ICA output waveforms is a fetal signal as well as a maternal signal.

In one method of determining which of the ICA output waveforms includes the maternal signal and the fetal signal, a fast Fourier transform for each ICA output waveform is computed. The FFT for each of the ICA output waveforms is classified and the significant frequency peaks and locations of such peaks are determined for the ICA output waveform for each of the plurality of channels.

Once all the FFTs for the ICA output waveforms have been determined and the frequency peaks identified, the system compares the peaks of the FFT for each of the ICA output waveforms to a known, typical maternal signal determined from a previous epoch. If the frequency peaks match the maternal signal for the previous epoch, the ICA output waveform is classified as being a maternal signal.

The system performs the same frequency matching to determine whether the ICA output waveform matches a known fetal signal from a previous epoch. If a particular ICA output waveform does not match either a known maternal signal or a known fetal signal, the ICA output waveform is classified as noise. Although one method of identifying which of the ICA output waveforms includes the maternal signal and the fetal signal is discussed, there are various other types of methods for identifying which of the ICA output waveforms include the maternal signal and the fetal signal.

Referring back to FIG. 4, the input waveforms from the maternal abdomen for the new, second epoch following the first epoch are fed into processing step 56. During step 56, the first transfer matrix that was determined from the first, previous epoch is applied to the input waveforms to generate a plurality of conditioned waveforms. The conditioned waveforms are transformed from the input waveforms by utilizing the transfer matrix that was determined in the previous epoch as shown by step 58.

Although the conditioned waveforms may not have the same degree of accuracy as the ICA output waveforms calculated over the entire second epoch, the conditioned waveforms determined in step 56 provide a relatively accurate estimation and can be calculated using the transfer matrix from the previous epoch on a continuous basis. Specifically, the input waveforms are fed into step 56 immediately following the first epoch such that the conditioned waveforms are calculated in step 56 during the entire time required to develop the second epoch. As an example, during the five seconds required to develop the second epoch, step 56 continuously receives the input waveforms and generates the conditioned waveforms over the entire five second period required for the second epoch.

As described previously, the system and method of the present disclosure assumes that the input channel waveforms are physically in the same input position for the ICA calculations from the first epoch to the second epoch. A further expectation, since the transfer matrix must contain properties that have to do with the physical and statistical properties of the input signals that do not change from epoch to epoch, is that the output signals from the ICA calculation will maintain the same positions. Specifically, the maternal source output position and the fetal source output position will tend to be the same since the transfer matrix calculated from the first epoch is used on the immediately following epoch. Based upon these assumptions, the transfer matrix calculated during a previous epoch can be applied to the input waveforms continuously during at least some portion of the second epoch. The continuous application of the transfer matrix from the previous epoch to the then-current epoch allows the system and method of the present disclosure to continuously calculate conditioned waveforms during the entire epoch. Although the assumption that the fetal and maternal signals do not change channels may be inaccurate for some epochs due to motion of either the fetus or the mother, the use of the transfer matrix from the previous epoch to continuously calculate the conditioned waveforms allows the system and method of the present disclosure to make continuous calculations prior to the calculation of the transfer matrix for the then-current epoch. The conditioned waveforms are fed to display 60. Thus, by utilizing the transfer matrix calculated during a previous epoch and applying the transfer matrix to the input waveforms received from the maternal abdomen, the system and method of the present disclosure can display conditioned waveforms continuously as they are received from the maternal patient.

Since the transfer matrix utilized in step 58 is the transfer matrix from the previous epoch, the transfer matrix utilized in step 58 should be continuously updated as each new epoch ends and the ICA algorithm is applied to the most current epoch in step 52.

In step 62, the system and method evaluates the transfer matrix coefficients for each of the independent sources on the sixteen input channels received from the maternal patient. The evaluation of the transfer coefficients for the most current transfer matrix (second transfer matrix) includes a comparison to the previous transfer matrix (first transfer matrix). In step 64, the system and method recognizes that the output channels have changed position and then rearranges the second transfer matrix based upon knowledge of the transfer matrix coefficients from the first transfer matrix as well as patterns and signals that are developed during the processing of analyzing sequential epochs. As an example, particular coefficients of the transfer matrix T may have certain properties that help in making the transfer process better in terms of outputting clearer fetal signals. For example, the coefficients for how to combine the channels to get the best fetal signal could have a very consistent pattern which can be measured and evaluated by correlation techniques. In other words, the fetal channel can be detected by looking at high correlations in the transfer matrix coefficient rows despite the fact that the fetal row has jumped to a new location. Thus, looking for similar coefficients within the first and second transfer matrix systems along different rows of the transfer matrix can help to sort the fetal and maternal signals even when a jump has occurred from one channel to another. Thus, in step 64, the new second transfer matrix may be rearranged based upon knowledge of the similar coefficients from the previous, first transfer matrix.

Next, in step 66, the system and method update the transfer matrix stored in the memory based upon the previous, first transfer matrix and the current, second transfer matrix.

After the transfer matrix has been updated to create the updated transfer matrix in step 66, the updated transfer matrix is utilized as the transfer matrix for conditioning the input waveforms following the second epoch, as illustrated in step 68. The updated transfer matrix, as shown by the dashed lines 70, is fed to step 58 such that the updated transfer matrix based upon the previous epoch is used to condition the input waveforms in step 56.

As can understood by the method shown and described in FIG. 4, the conditioned waveforms calculated in step 56 are calculated utilizing the transfer matrix calculated during the most recent previous epoch. The transfer matrix calculated from the most previous epoch is utilized to condition the input waveforms, which can then be continuously displayed on the display 60.

The display 60 can be utilized to display selected conditioned waveforms calculated in step 56. As an example, in step 54, the system determines which channel best represents the maternal signal source and which channel best represents the fetal signal source. Based upon the determination of which channels are maternal and fetal signals, the display 60 can be configured to display the condition signals for only those channels that include either the fetal signal or the maternal signal, or both. Since the input waveforms are modified in step 56 on a continuous basis, the display shows the conditioned waveform on a real time continuous basis.

As can best be understood, since the conditioned waveforms are shown continuously on the display 60, the length of the epoch can be adjusted or modified during operation, since the waveforms are displayed continuously, rather than at the end of a predefined epoch.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of identifying a fetal ECG signal from a plurality of input waveforms from a maternal patient, comprising the steps of:
    positioning a plurality of ECG electrodes on an abdomen of the maternal patient;
    obtaining a set of input waveforms from the maternal patient through the ECG electrodes for a plurality of epochs;
    storing the plurality of input waveforms for a first epoch;
    applying an independent component analysis (ICA) algorithm to the stored input waveforms for the first epoch to generate a plurality of ICA output waveforms, wherein the ICA algorithm generates a first transfer matrix for the first epoch;
    continuously applying the first transfer matrix to the plurality of input waveforms as the plurality of input waveforms are obtained following the first epoch to generate a plurality of conditioned waveforms; and
    continuously displaying at least one of the conditioned waveforms following the first epoch in real time.

2. The method of claim 1 wherein the conditioned waveforms are continuously displayed.

3. The method of claim 2 wherein only selected waveforms of the conditioned waveforms are displayed.

4. The method of claim 1 wherein the first epoch has a determined time length.

5. The method of claim 1 wherein the first epoch has a variable time length.

6. The method of claim 1 further comprising the steps of:
    storing the plurality of input waveforms for a second epoch following the first epoch;
    applying the ICA algorithm to the stored input waveforms for the second epoch to generate a plurality of ICA output waveforms for the second epoch and a second transfer matrix for the second epoch;
    combining the first transfer matrix and the second transfer matrix;
    generating an updated transfer matrix based upon the combination of the first transfer matrix and the second transfer matrix; and
    continuously applying the updated transfer matrix to the plurality of input waveforms following the second epoch.

7. The method of claim 6 wherein the updated transfer matrix is generated based upon an average of corresponding coefficients within the first transfer matrix and the second transfer matrix.

8. The method of claim 6 wherein the updated transfer matrix is generated based upon the most current epoch and the previous epoch.

9. The method of claim 1 further comprising the steps of:
    determining the conditioned waveform that contains a fetal ECG source; and
    displaying only the conditioned waveform as the fetal ECG signal.

10. A method of separating a fetal ECG signal from a plurality of input waveforms received from a plurality of ECG electrodes attached to an abdomen of a maternal patient, the method comprising the steps of:
    receiving the plurality of input waveforms from the electrodes, each input waveform being received as one of a plurality of channels each associated with a set of the plurality of electrodes;
    storing the plurality of input waveforms for a first epoch;
    applying an independent component analysis (ICA) algorithm to the plurality of stored input waveforms, wherein the ICA algorithm generates a first transfer matrix for the first epoch and a plurality of ICA output waveforms;
    continuously applying the first transfer matrix to the plurality of input waveforms as the plurality of input waveforms are obtained following the first epoch to generate a plurality of conditioned waveforms; and
    continuously displaying at least the conditioned waveform that represents the fetal ECG signal following the first epoch.

11. The method of claim 10 wherein the conditioned waveforms are continuously displayed.

12. The method of claim 10 further comprising the steps of:
    determining the channel that contains a fetal ECG source; and
    displaying only the conditioned waveform for the determined channel as the fetal ECG signal.

13. The method of claim 10 further comprising the steps of:
    storing the plurality of input waveforms for a second epoch following the first epoch;
    applying the ICA algorithm to the stored input waveforms for the second epoch to generate a plurality of ICA output waveforms and a second transfer matrix for the second epoch;
    combining the first transfer matrix and the second transfer matrix;
    generating an updated transfer matrix based upon the combination of the first transfer matrix and the second matrix; and
    continuously applying the updated transfer matrix to the plurality of input waveforms following the second epoch.

14. The method of claim 13 wherein the updated transfer matrix is generated based upon an average of the first transfer matrix and the second transfer matrix.

15. The method of claim 13 wherein the updated transfer matrix is generated based upon the most current epoch and the previous epoch.

16. The method of claim 10 further comprising the steps of:

determining the output channel that contains a maternal ECG source; and displaying the conditioned waveform for the determined channel as the maternal ECG signal.

17. The method of claim 16 wherein the conditioned waveforms that include both the fetal ECG signal and the maternal ECG signal are continuously displayed.

18. The method of claim 13 wherein the updated transfer matrix is generated as a combination of previous transfer coefficients based upon a filtering of the transfer matrix coefficients from any set of previous epochs.

* * * * *

UNITED STATES PATENT AND TRADEMARK OFFICE
CERTIFICATE OF CORRECTION

PATENT NO. : 7,831,300 B2
APPLICATION NO. : 12/034129
DATED : November 9, 2010
INVENTOR(S) : Kolluri et al.

Page 1 of 1

It is certified that error appears in the above-identified patent and that said Letters Patent is hereby corrected as shown below:

In Column 1, Line 64, delete "epoch" and insert -- epoch. --, therefor.

In Column 13, Line 1, in Claim 16, after "the" delete "output".

Signed and Sealed this
Thirty-first Day of May, 2011

David J. Kappos
*Director of the United States Patent and Trademark Office*